United States Patent
Xia et al.

(10) Patent No.: US 12,129,315 B2
(45) Date of Patent: Oct. 29, 2024

(54) **MONOMERIC POLYSACCHARIDE ISOLATED FROM *AURICULARIA AURICULA*-JUDAE, AND PREPARATION METHOD AND USE THEREOF**

(71) Applicant: Jun Liang, Harbin (CN)

(72) Inventors: Yonggang Xia, Harbin (CN); Jun Liang, Harbin (CN); Junxi Liu, Harbin (CN); Siliang Jiang, Harbin (CN); Zihao Rao, Harbin (CN)

(73) Assignee: Jun Liang, Harbin (CN)

( * ) Notice: Subject to any disclaimer, the term of this patent is extended or adjusted under 35 U.S.C. 154(b) by 0 days.

(21) Appl. No.: 18/222,492

(22) Filed: Jul. 17, 2023

(65) Prior Publication Data
US 2024/0026038 A1     Jan. 25, 2024

(30) Foreign Application Priority Data
Jul. 17, 2022 (CN) .......................... 202210854670.4

(51) Int. Cl.
*C08B 37/00* (2006.01)
*A61K 31/715* (2006.01)
*A61P 11/00* (2006.01)

(52) U.S. Cl.
CPC ........ *C08B 37/0003* (2013.01); *A61K 31/715* (2013.01); *A61P 11/00* (2018.01); *C08B 37/006* (2013.01)

(58) Field of Classification Search
CPC .................................................... A61K 36/07
See application file for complete search history.

(56) References Cited

PUBLICATIONS

Chen, N. et al., "Polysaccharides from Auricularia auricula: Preparation, structural features and biological activities", 2020, Carbohydrate Polymers, vol. 247, pp. 1-28 (Year: 2020).*
Leong, Y.K. et al., "Extraction of polysaccharides from edible mushrooms: Emerging technologies and recent advances", 2021, Carbohydrate Polymers, vol. 251, pp. 1-16 (Year: 2021).*
Han Xiao-Qian, Study on The Process to Seperate Antioxidant Polysaccharides from Auricularia Auricula by Radial Chromatography, Dissertation Submitted to Zhejiang Gongshang University for Master's Degree of Engineering, 2010, pp. 1-67.

* cited by examiner

*Primary Examiner* — Bahar Craigo
(74) *Attorney, Agent, or Firm* — Bayramoglu Law Offices LLC

(57) ABSTRACT

A monomeric polysaccharide isolated from *Auricularia auricula-judae* (*A. auricula*), and a preparation method and use thereof are provided. The monomeric polysaccharide includes xylose, glucuronic acid, galactose, glucose, and mannose. The present disclosure further provides a structure and a preparation method of the monomeric polysaccharide isolated from *A. auricula*, and the preparation method adopts a plurality of chromatographic techniques. The monomeric polysaccharide isolated from *A. auricula* in the present disclosure is high-acetyl glucuronoxylogalactoglucomannan. The monomeric polysaccharide can reduce percentages of eosinophils, neutrophils, and lymphocytes in a lung lavage solution of a $SiO_2$ dust-induced silicosis model mouse, significantly reduce levels of oxidative and inflammatory factors such as SOD, HYP, IL-6, and TNF-α in a $SiO_2$ dust-induced silicosis model group in a dose-dependent manner, exhibit a protective effect for an experimental $SiO_2$ dust-induced silicosis model mouse.

1 Claim, 12 Drawing Sheets

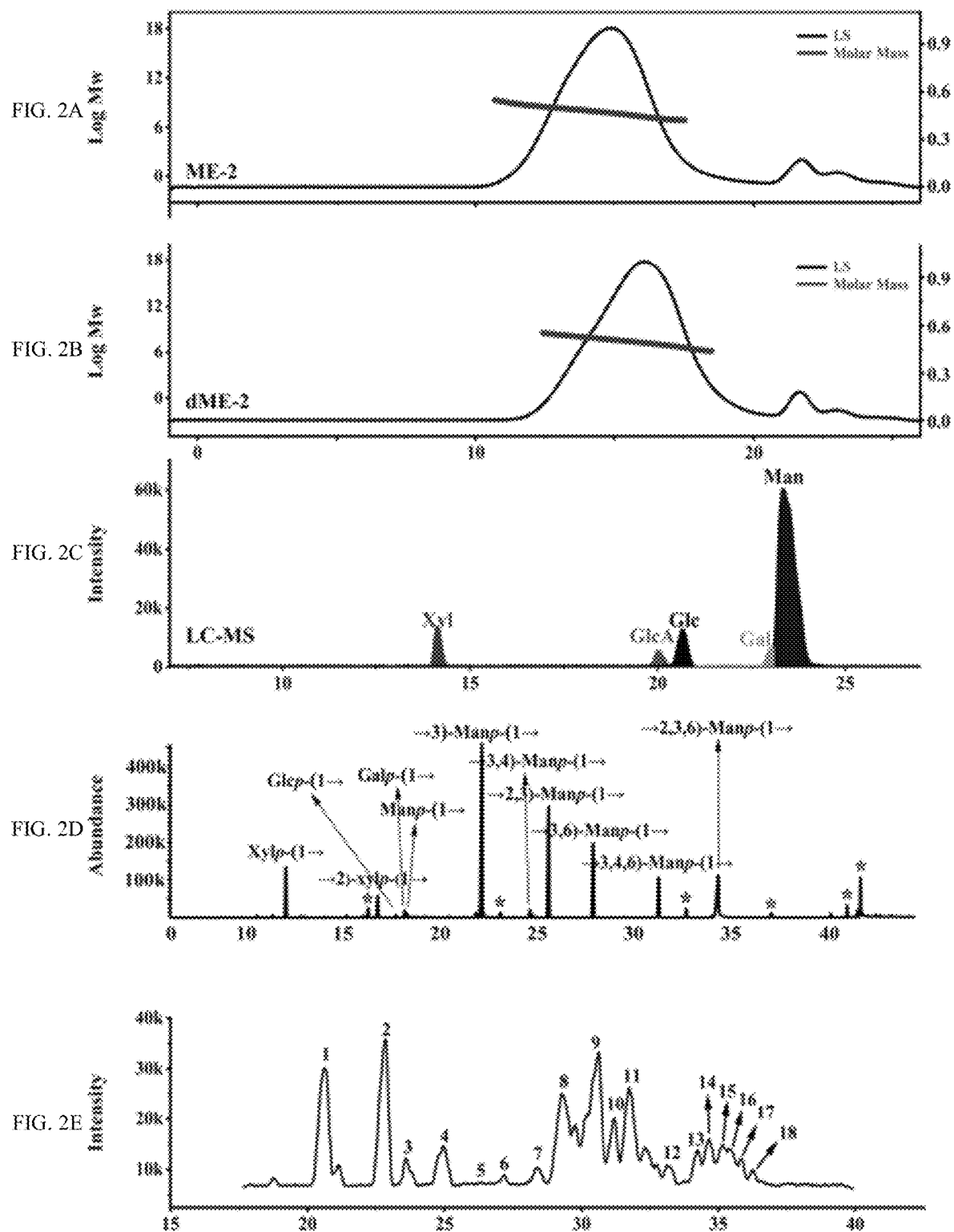

Control group

Model group

Positive drug group

Low dose group

Medium dose group

High dose group

Control group

Model group

Positive drug group

Low dose group

Medium dose group

High dose group

MONOMERIC POLYSACCHARIDE ISOLATED FROM *AURICULARIA AURICULA*-JUDAE, AND PREPARATION METHOD AND USE THEREOF

CROSS REFERENCE TO THE RELATED APPLICATIONS

This application is based upon and claims priority to Chinese Patent Application No. 202210854670.4, filed on Jul. 17, 2022, the entire contents of which are incorporated herein by reference.

TECHNICAL FIELD

The present disclosure relates to a monomeric polysaccharide, and in particular to a monomeric polysaccharide isolated from *Auricularia auricula-judae* (*A. auricula*) and a preparation method thereof. The present disclosure further relates to a use of the monomeric polysaccharide in preparation of a drug for preventing or treating silicosis, and belongs to the fields of monomeric polysaccharides and applications thereof.

BACKGROUND

*A. auricula* is a delicious and medicinal edible mushroom. There is a long history of eating *A. auricula* in China, and modern pharmacological studies have shown that polysaccharides in *A. auricula* have pharmacological activities such as anti-coagulation, anti-tumor, and immunoregulation. So far, the isolation and purification of polysaccharides in *A. auricula* has been conducted by researchers mostly through water extraction-alcohol precipitation, a protease reaction, removal of proteins and pigments with chemical reagents, or the like. The current isolation processes are complicated, cause heavy pollution in the environment, and easily destroy the chemical structure of the native polysaccharides in *A. auricula*, which affects and change biological activities of the polysaccharides, and is not conducive to large-scale industrial production.

Because polysaccharides in *A. auricula* have a large molecular weight, a high acetyl content, and a highly-complex structure, the research on characterization of structures of the polysaccharides is extremely challenging. So far, most of the research on the structure of polysaccharides in *A. auricula* has been limited to study of the crude polysaccharides. Although there are sporadic reports about structural characteristics of monomeric polysaccharides, most of the reports are limited to small-molecular-weight polysaccharides (about 70.0 kDa) in *A. auricula*. The chemical fine structure repeating units of the polysaccharides cannot be clearly and accurately elucidated, and involvement of large-molecular-weight native polysaccharides in *A. auricula* is not known, which seriously hinders the further upgrading of the *A. auricula* industry in the pharmaceutical field. Since the structures of the monomeric polysaccharides cannot be clearly characterized, it cannot be determined whether there is structural novelty in a monomeric polysaccharide, which affects subsequently related studies and applications.

SUMMARY

A first objective of the present disclosure is to provide a monomeric polysaccharide isolated from *A. auricula*.

A second objective of the present disclosure is to provide a method for isolating a monomeric polysaccharide from *A. auricula*.

A third objective of the present disclosure is to provide a use of the monomeric polysaccharide in preparation of a drug for preventing or treating silicosis.

The above objectives of the present disclosure are achieved by the following technical solutions.

In a first aspect, the present disclosure provides a monomeric polysaccharide ME-2 isolated from *A. auricula*, where the monomeric polysaccharide is high-acetyl glucuronoxylogalactoglucomannan; and the monomeric polysaccharide includes xylose (Xyl), glucuronic acid (GlcA), galactose (Gal), glucose (Glc), and mannose (Man); and the Xyl, GlcA, Gal, Glc, Man are in a theoretical molar ratio of 3:4:1:1:11.

Further, chemical structural characteristics of the monomeric polysaccharide ME-2 provided by the present disclosure are as follows: white flocci, flexible chain conformation, and high solubility in water; absolute molecular weight $M_w$: 260 kDa, characteristic viscosity $[\eta]$: 370 mL/g, root mean square (RMS) radius of gyration $R_g$: 42.6 nm, and conformation parameter $\rho$: 1.64; and acetyl content: 18% ($M^{Acetyl}/M_w \times 100\%$).

Further, the monomeric polysaccharide ME-2 includes the following residues: →3)-Manp-(1→, →2,3)-Manp-(1→, >2,3,6)-Manp-(1→, →3,6)-Manp-(1→, Manp-(1→, Glcp-(1→, GlcAp-(1→, Xylp-(1→, and Galp-(1→; and the →3)-Manp-(1→, →2,3)-Manp-(1→, →2,3,6)-Manp-(1→, →3,6)-Manp-(1→, Manp-(1→, Glcp-(1→, GlcAp-(1→, Xylp-(1→, and Galp-(1→ are in a theoretical ratio of 3:1:3:3:1:1:4:3:1.

Further, the chemical fine structure repeating unit of the monomeric polysaccharide ME-2 is as follows:

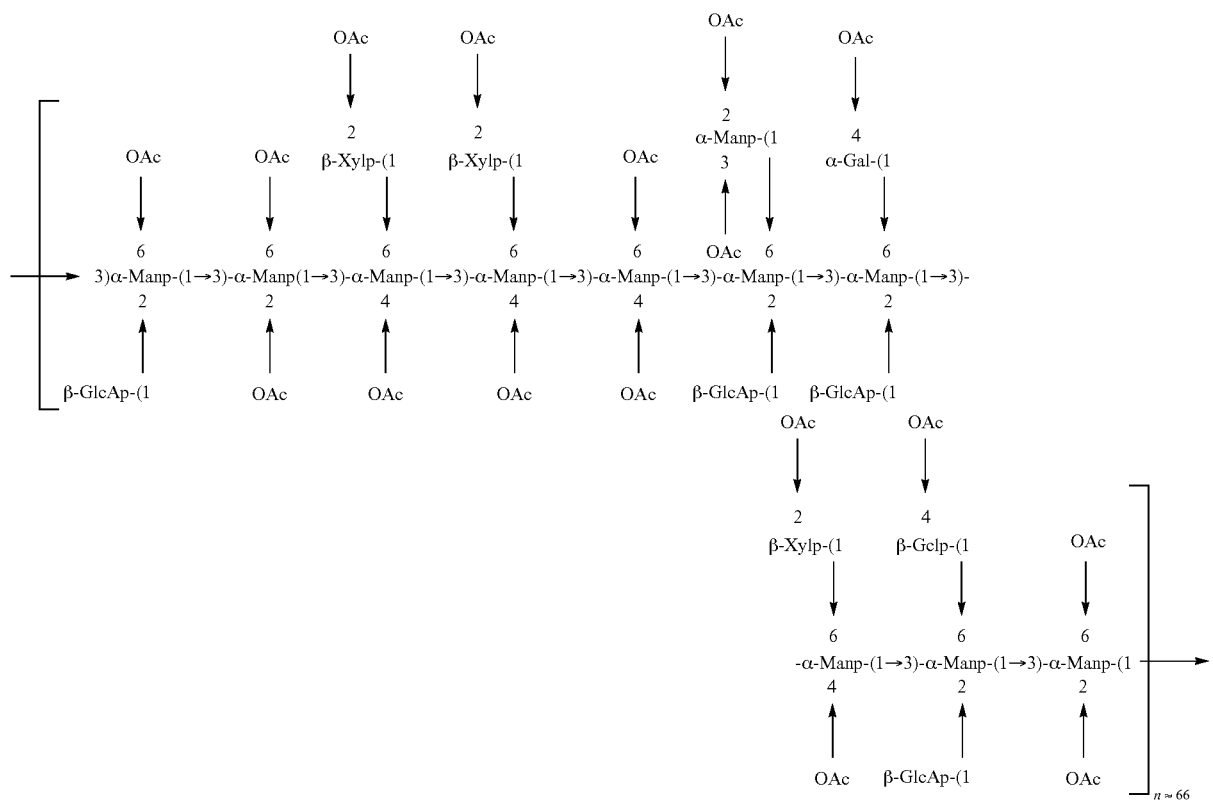

In a second aspect, the present disclosure provides a method for isolating the monomeric polysaccharide from *A. auricula*, including:
(1) with water as an extraction solvent, conducting heat reflux extraction (HRE) to obtain an *A. auricula* extract-containing aqueous solution;
(2) subjecting the *A. auricula* extract-containing aqueous solution to adsorption with a macroporous adsorption resin column to remove substances such as pigments and proteins, and subjecting the macroporous adsorption resin column to elution with an eluent to obtain an *A. auricula* extract-containing aqueous eluate;
(3) subjecting the *A. auricula* extract-containing aqueous eluate to dialysis with an ultrafiltration (UF) or dialysis bag to obtain refined total polysaccharides of *A. auricula*; and
(4) treating the refined total polysaccharides of *A. auricula* through column chromatography to obtain a refined polysaccharide I of *A. auricula*, and purifying the refined polysaccharide I with an anion exchange gel column to obtain a refined monomeric polysaccharide.

As a preferred specific embodiment of the present disclosure, in step (2), the macroporous adsorption resin column is an AB-8 macroporous adsorption resin; the eluent is distilled water, and during the elution, the distilled water is used at an amount six times a volume of the column; and an end point is detected by a phenol-sulfuric acid method.

As a preferred specific embodiment of the present disclosure, in step (3), the *A. auricula* extract-containing aqueous eluate is preferably subjected to an interception treatment with a 3 kDa UF chromatographic column to obtain the refined total polysaccharides of *A. auricula*, where a sample concentration is 7:1 (water volume (mL): medicinal material weight (g)) and a UF pressure is 2 Mpa.

As a preferred specific embodiment of the present disclosure, in step (4), the refined total polysaccharides of *A. auricula* are first treated with an Amber-lite FPA90-Cl$^-$ anion exchange resin to obtain the refined polysaccharide I of *A. auricula*, and then subjected to refinement and purification with a DEAE-650M anion exchange chromatographic column to obtain the refined monomeric polysaccharide.

More preferably, when the refined total polysaccharides of *A. auricula* are first treated with the Amber-lite FPA90-Cl$^-$ anion exchange resin to obtain the refined polysaccharide I of *A. auricula*, elution is conducted with distilled water in a volume four times a volume of a column and 1 mol/L NaCl in a volume two times the volume of the column, and an eluate of the distilled water is collected to obtain the refined polysaccharide I of *A. auricula*; and when the refined polysaccharide I is subjected to refinement and purification with the DEAE-650M anion exchange chromatographic column to obtain the refined monomeric polysaccharide, elution is conducted with distilled water and 0.5 mol/L NaCl, and an eluate of the 0.5 mol/L NaCl is collected to obtain the refined monomeric polysaccharide.

The monomeric polysaccharide isolated from *A. auricula* provided in the present disclosure can reduce percentages of eosinophils, neutrophils, and lymphocytes in a lung lavage solution of a $SiO_2$ dust-induced silicosis model mouse, and significantly reduce levels of oxidative and inflammatory factors such as SOD, HYP, IL-6, and TNF-α in a $SiO_2$ dust-induced silicosis model group in a dose-dependent manner, finally indicating that the monomeric polysaccharide isolated from *A. auricula* has a protective effect for an experimental $SiO_2$ dust-induced silicosis model mouse.

Therefore, the monomeric polysaccharide isolated from *A. auricula* provided in the present disclosure can be used in preparation of a drug for treating or preventing silicosis.

The present disclosure provides a pharmaceutical composition for controlling silicosis, including: a therapeutically effective amount of the monomeric polysaccharide and a pharmaceutically acceptable adjuvant or carrier.

The pharmaceutical composition is prepared into a suitable clinical preparation in accordance with a conventional preparation method of a traditional Chinese medicine (TCM), and is preferably prepared into an oral preparation; and a dosage form of the preparation includes a granule, an effervescent agent, an oral liquid, a spray, a capsule, an ointment, a syrup, a tablet, or another conventional clinical dosage form.

The adjuvant or carrier of the present disclosure refers to a conventional adjuvant or carrier in the pharmaceutical field, such as a diluent, a disintegrating agent, a lubricant, an excipient, a binder, a glidant, a filler, and a surfactant. In addition, another additive such as a flavoring agent and a sweetening agent may be added to the composition. The diluent may be one or more components that increase a weight and volume of a tablet, and common diluents include lactose, starch, pregelatinized starch, microcrystalline cellulose (MCC), sorbitol, mannitol, and inorganic calcium salts, among which the lactose, the starch, and the MCC are the most common. The disintegrating agent may be one or a mixture of two or more selected from the group consisting of crosslinked polyvinylpyrrolidone (PVP) (a proportion of a weight of the crosslinked PVP in a total weight of the composition is 2% to 6%), crosslinked sodium carboxymethyl cellulose (Na-CMC) (a proportion of a weight of the crosslinked Na-CMC in the total weight of the composition is 2% to 6%), alginic acid (a proportion of a weight of the alginic acid in the total weight of the composition is 2% to 5%), and MCC (a proportion of a weight of the MCC in the total weight of the composition is 5% to 15%). The lubricant includes one or a mixture of two or more selected from the group consisting of stearic acid, sodium stearate, magnesium stearate, calcium stearate, polyethylene glycol (PEG), talc powder, and hydrogenated vegetable oil (HVO). The lubricant is added at an amount in a range of 0.10% to 1% (a proportion of the lubricant in the total weight of the composition) and generally in a range of 0.25% to 0.75%. The binder may be one or more ingredients conducive to granulation; and the binder can be a mixture of a starch slurry (10% to 30%, which is a proportion of a weight of the starch slurry in a total weight of the binder), hydroxypropyl methylcellulose (HPMC) (2% to 5%, which is a proportion of a weight of the HPMC in the total weight of the binder), and PVP (2% to 20%, which is a proportion of a weight of the PVP in the total weight of the binder), and can be preferably an aqueous solution of PVP in ethanol. The glidant may be one or a mixture of two or more selected from the group consisting of micronized silica gel, talc powder, and magnesium trisilicate. The surfactant may be one or more components that can improve the wettability and increase the drug dissolution, and may be commonly sodium dodecyl sulfate (SDS) (SDS is commonly used in a range of 0.2% to 6%, which is a proportion of a weight of the SDS in the total weight of the composition).

BRIEF DESCRIPTION OF THE DRAWINGS

FIGS. 2A-2E show spectral identification results of a monomeric polysaccharide ME-2 of *A. auricula*, where FIG. 2A shows a multi-angle laser light scatting (MALLS) pattern of the monomeric polysaccharide ME-2; FIG. 2B shows an MALLS pattern of a deacetylated monomeric polysaccharide ME-2; FIG. 2C shows a monosaccharide composition of the monomeric polysaccharide ME-2; FIG. 2D shows an analysis chart of alkaline methylation of the monomeric polysaccharide ME-2; and FIG. 2E shows a total ion chromatogram of free radical degradation of the monomeric polysaccharide ME-2.

FIG. 3A shows a hydrogen NMR spectrum of the monomeric polysaccharide ME-2; FIG. 3B shows a carbon NMR spectrum of the monomeric polysaccharide ME-2; FIG. 3C shows a hydrogen NMR spectrum of a deacetylated monomeric polysaccharide ME-2; FIG. 3D shows a carbon NMR spectrum of the deacetylated monomeric polysaccharide ME-2; and FIG. 3E shows a DEPT-135 carbon NMR spectrum of the deacetylated monomeric polysaccharide ME-2.

FIG. 4A shows a structure of the deacetylated monomeric polysaccharide ME-2 and FIG. 4B shows a structure of the monomeric polysaccharide ME-2.

DETAILED DESCRIPTION OF THE EMBODIMENTS

Figure 1:
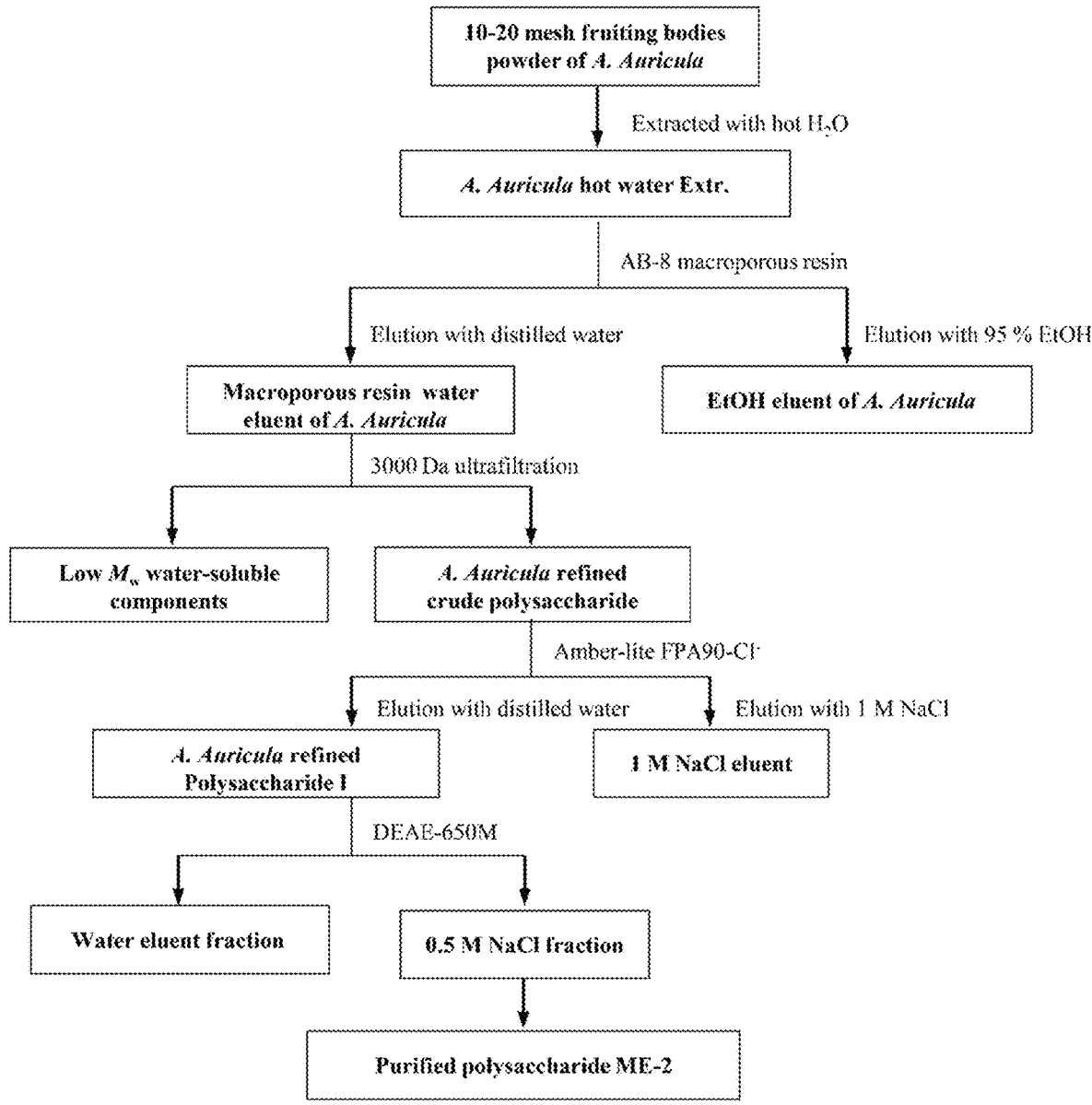
FIG. 1 is a flow chart of a preparation process of a monomeric polysaccharide of *A. auricula*.
Figure 3A:
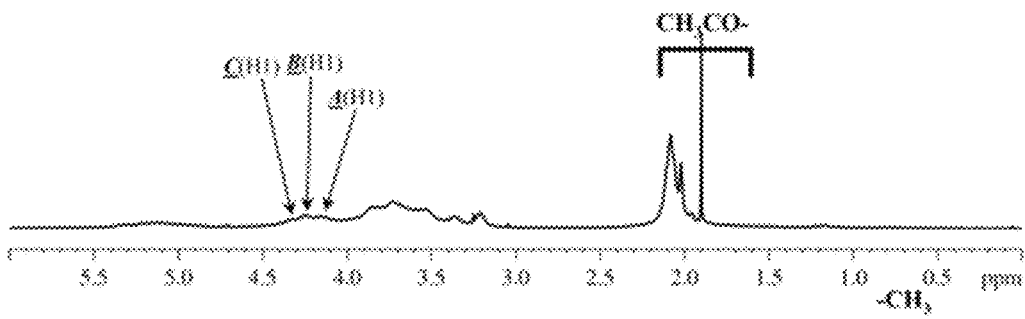
FIGS. 3A-3E show hydrogen nuclear magnetic resonance (NMR) spectra or carbon NMR spectra of a monomeric polysaccharide ME-2 of *A. auricula*, where
Figure 3B:
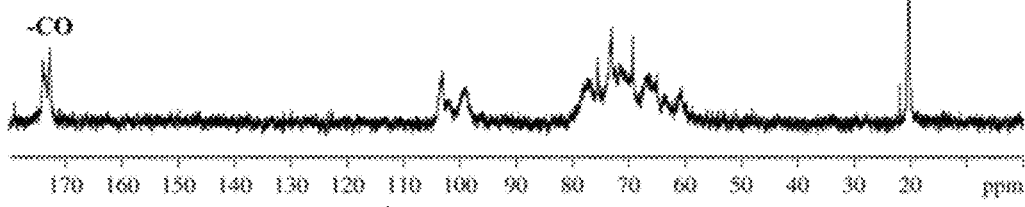
Figure 3C:
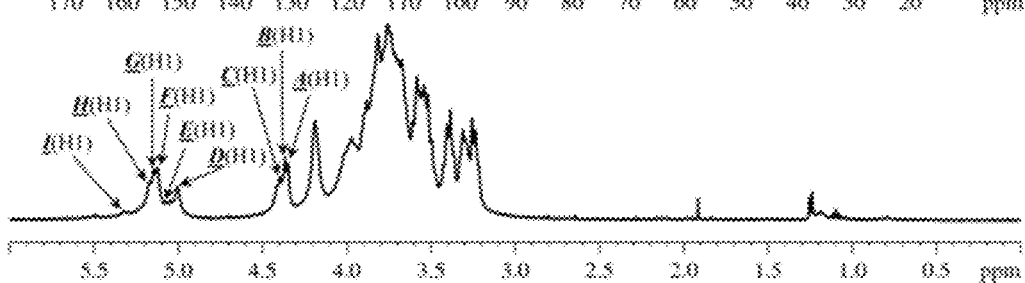
Figure 3D:
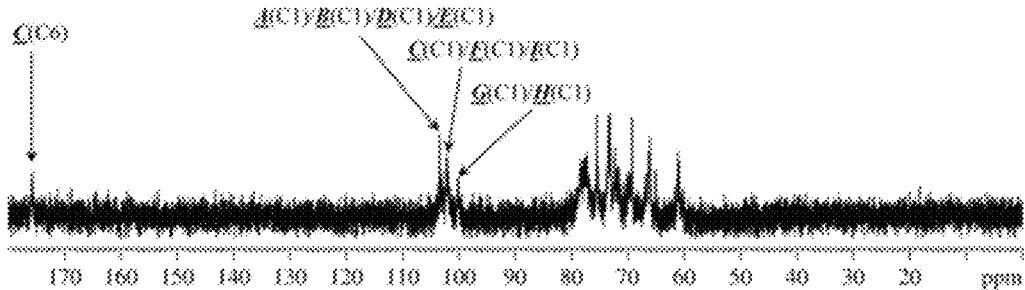
Figure 3E:
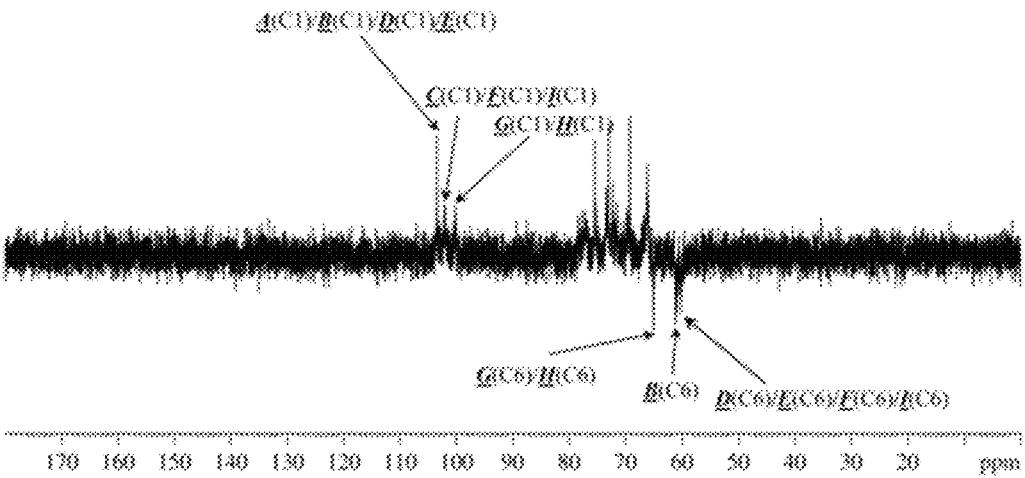

The present disclosure will be further described below in conjunction with specific examples, and the advantages and features of the present disclosure will become clear from the description. However, these examples are only exemplary and do not constitute any limitation to the scope of the present disclosure. Those skilled in the art should appreciate that modifications and substitutions can be made to the details and forms of the present disclosure without departing from the spirit and scope of the present disclosure, but these modifications and substitutions fall within the protection scope of the present disclosure.

Example 1 Preparation and Characterization of a Monomeric Polysaccharide ME-2 of *A. auricula*

About 5 kg of crushed *A. auricula* was taken; 250 g of the crushed *A. auricula* was taken each time, then 8 L of distilled water was added, extraction was conducted for 3 h, a residue was filtered out with a gauze, and the extraction was repeated 2 times; and resulting *A. auricula* extract-containing aqueous solutions were combined. A resulting *A. auricula* extract-containing aqueous solution was subjected to adsorption for 12 h with an AB-8 macroporous adsorption resin, and then elution was conducted with distilled water until an eluate was tested by a phenol-sulfuric acid method to be light-yellow (this method could remove some substances such as pigments and proteins in polysaccharides of *A. auricula*). A resulting *A. auricula* extract-containing aqueous eluate was further subjected to purification with a 3,000 Da UF chromatographic column to remove oligosaccharides and soluble salts to obtain refined total polysaccharides of *A. auricula*. The refined total polysaccharides of *A. auricula* were treated with an anion exchange resin (Amber-lite FPA90-Cl⁻), where elution was first conducted with distilled water until an elution end point was detected by a phenol-sulfuric acid method, and then conducted with 1 M NaCl to further allow decoloration and protein removal, and an eluate of the distilled water was collected to obtain 500 g of a refined polysaccharide I of *A. auricula*, with an extraction ratio of 10.10%. The refined polysaccharide I of *A. auricula* was dissolved in water and further subjected to purification with a DEAE-650M anion exchange chromatographic column (mobile phases of distilled water and 0.5 mol/L NaCl were adopted sequentially), and an eluate of the 0.5 mol/L NaCl was collected to obtain a refined monomeric polysaccharide of *A. auricula*, which was recorded as ME-2.

The ME-2 was white flocculent and very soluble in water. Through a multi-cascade technology of size exclusion chromatography-multi-angle laser light scatting-viscosity-refractive index detector (SEC-MALLS-VIS-RID) (FIG. 2A), it was determined that the ME-2 had an absolute molecular weight $M_w$ of 260 kDa, a characteristic viscosity [η] of 370 mL/g, an RMS radius of gyration $R_g$ of 42.6 nm, and a conformation parameter p of 1.64, indicating a flexible chain conformation. Through an SEC-MALLS-RID-based absolute molecular weight on-line detection technology, a difference between absolute molecular weights of the ME-2 before and after deacetylation ($M^{Acetyl}/M_w \times 100\%$) was calculated to obtain an acetyl content of the ME-2, which was 18%.

The monosaccharide composition analysis was conducted by liquid chromatography-multireaction monitoring-mass spectrometry (LC-MRM-MS) (FIG. 2C). It was determined by a glyconitrile acetate derivation method that the ME-2 included the monosaccharides of Xyl, GlcA, Gal, Glc, and Man in an experimental ratio of about 10.2:1.48:1:1.92:23.7, indicating that the ME-2 mainly included Man, and also included a specified amount of Xyl, GlcA, Gal, and Glc.

Methylation analysis was conducted by gas chromatography-mass spectrometry (GC-MS). The ME-2 was partially methylated into a glycol acetate derivative with a sodium methoxide iodomethane alkaline system, and then it was determined that the ME-2 included the following residues: Xylp-(1→ (7.01%), →2)-Xylp-(1→ (2.29%), Manp-(1→ (0.68%), Galp-(1→ (0.71%), Glcp-(1→ (0.27%), →3)-Manp-(1→ (36.68%), →3,4)-Manp-(1→ (3.50%), →2,3)-Manp-(1→ (25.06%), →3,6)-Manp-(1→ (12.51%), →3,4,6)-Manp-(1→ (5.38%), →2,3,6)-Manp-(1→ (5.90%), and trace amounts of →4)-Glcp-(1→ and →4)-Galp-(1→.

It should be noted that, although Glcp-(1→ is also detected by GC-MS in the above alkaline methylation analysis, a content of Glcp-(1→ determined in the above alkaline methylation analysis is significantly lower than a content of Glcp-(1→ determined in the monosaccharide composition analysis, and this contradiction may be related to a spatial environment in which Glc residues in the ME-2 are located. A spatial position of a Glc residue may be close to a spatial position of a GlcA residue, which is not conducive to the release of Glc residues during hydrolysis of fully-methylated polysaccharide. Therefore, the ME-2 was further subjected to GlcA carboxyl-reduction to obtain a carboxyl-reduced ME-2 derivative, which was named r-ME-2; and an infrared (FT-IR) spectrum of the carboxyl-reduced ME-2 derivative was tested, where a carbonyl signal peak at 1,740 cm-1 completely disappeared, indicating that the carboxyl was successfully reduced. Then, the r-ME-2 was subjected to the above GC-MS alkaline methylation analysis, and it was determined that the r-ME-2 included the following residues: Xylp-(1→ (4.49%), Glcp-(1→ (20.32%), →3)-Manp-(1→ (35.72%), →3,4)-Manp-(1→ (4.88%), →2,3)-Manp-(1→ (22.26%), and →3,6)-Manp-(1→ (12.33%), which was consistent with an expectation. A content of the Glcp-(1→ was significantly increased, which may be attributed to GlcAp-(1→ or may be attributed to Glcp-(1→. Since there is no steric hindrance of GlcA after reduction, it is possible that the original Glc residues in the r-ME-2 can be completely released.

In addition, since the ME-2 included a large number of acetyl groups and the acetyl groups in a molecular structure of the ME-2 are completely removed through substitution during the alkaline methylation, in order to further determine linking positions of the acetyl groups, the ME-2 was subjected to non-alkaline methylation analysis according to a method in the literature, where the ME-2 was partially methylated with a trimethyl phosphate (TMP)-methyl trifluoromethanesulfonate (MTFMS) system to obtain a glycol acetate derivative, and it was determined that the ME-2 included the following residues: →2,3)-Manp-(1→, →3,4,6)-Manp-(1→, Xylp-(1→, and →2)-Xylp-(1→. Although the non-alkaline methylation analysis can provide partial acetyl linking sites, it is still insufficient to allow clear description. Therefore, according to the literature, the ME-2 was subjected to deacetylation to obtain a deacetylated product d-ME-2, and then the deacetylated product was subjected to alkaline methylation. Results showed that the d-ME-2 included the following residues: Xylp-(1→, Manp-(1→, Glcp-(1→, Galp-(1→, →3)-Manp-(1→, →2,3)-Manp-(1→, →3,6)-Manp-(1→, and →2,3,6)-Manp-(1→. It can be determined through comparison of all methylation analysis results that possible linking sites of acetyl are positions C-2 and C-4 of Man, positions C-4 of Glc and Gal, and position C-2 of Xyl.

In ¹H-NMR and ¹³C-NMR of the ME-2, high-intensity signals at $δ_H$ 2.0 and $δ_C$ 20.0 can meaninglessly be attributed to acetyl signals. Because the high-intensity acetyl signals seriously affected the signal attribution of each sugar residue, the acetyl in the ME-2 was further removed through alkaline hydrolysis to obtain a deacetylated ME-2 derivative, which was named d-ME-2; and an FT-IR spectrum of the deacetylated ME-2 derivative was tested, where a carbonyl signal peak at 1,740 cm-1 disappeared, indicating successful deacetylation. Then, ¹H-NMR and ¹³C-NMR of the d-ME-2 were further tested, where there were basically no obvious signal peaks at $δ_H$ 2.0 and $δ_C$ 20.0, further indicating the successful deacetylation of the d-ME-2.

In a terminal proton region, the nine terminal protons $δ_H$ 5.33 (1H, s), $δ_H$ 5.17 (1H, s), $δ_H$ 5.15 (1H, s), $δ_H$ 5.12 (1H, s), $δ_H$ 5.05 (1H, s), $δ_H$ 5.00 (1H, s), $δ_H$ 4.40 (1H, s), $δ_H$ 4.37 (1H, s), and $δ_H$ 4.35 (1H, s) could be attributed to Galp-(1→, →2,3,6)-Manp-(1→, →3,6)-Manp-(1→, →2,3)-Manp-(1→, Manp-(1→, →3)-Manp-(1→, GlcAp-(1→, Glcp-(1→, and Xylp-(1→, respectively. Since chemical shifts of terminal protons of the Galp-(1→, →2,3,6)-Manp-(1→, →3,6)-Manp-(1→, →2,3)-Manp-(1→, Manp-(1→, →3)-Manp-(1→, GlcAp-(1→, Glcp-(1→, and Xylp-(1→ were $\delta_H$ 5.33 (1H, s), $\delta_H$ 5.17 (1H, s), $\delta_H$ 5.15 (1H, s), $\delta_H$ 5.12 (1H, s), OH 5.05 (1H, s), 5.00 (1H, s), OH 4.40 (1H, s), OH 4.37 (1H, s), and $\delta_H$ 4.35 (1H, s), respectively, it was further determined that terminal configurations of the Galp-(1→, →2,3,6)-Manp-(1→, →3,6)-Manp-(1→, →2,3)-Manp-(1→, Manp-(1→, →3)-Manp-(1→, GlcAp-(1→, Glcp-(1→, and Xylp-(1→ were α, α, α, α, α, α, β, β, and β, respectively.

Figure 5A:
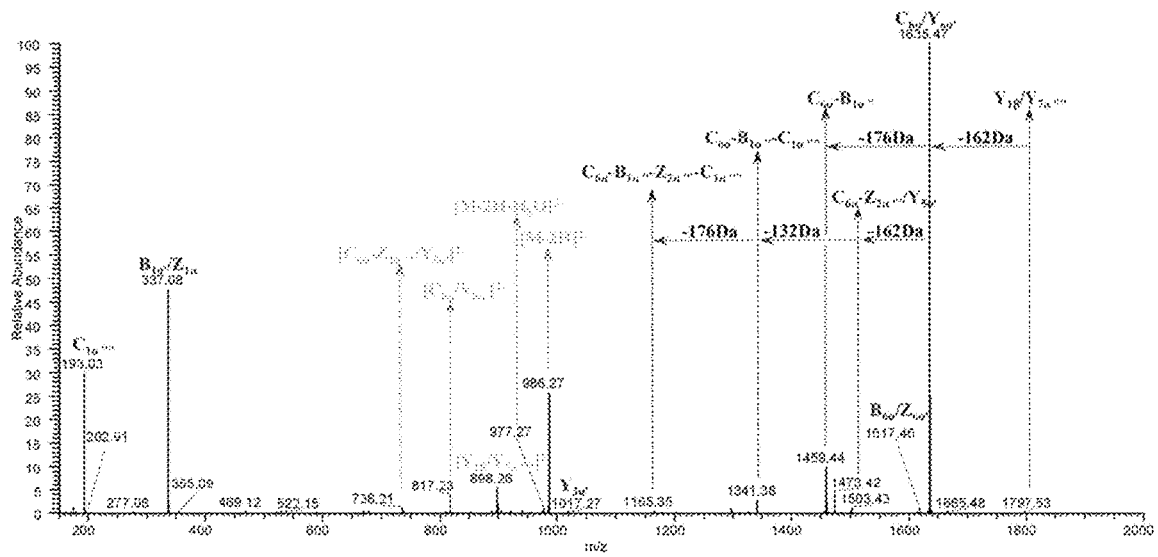
FIGS. 5A-5C show an analysis example of ion fragments resulting from free radical degradation of the monomeric polysaccharide ME-2 of *A. auricula*.
Figure 5B:
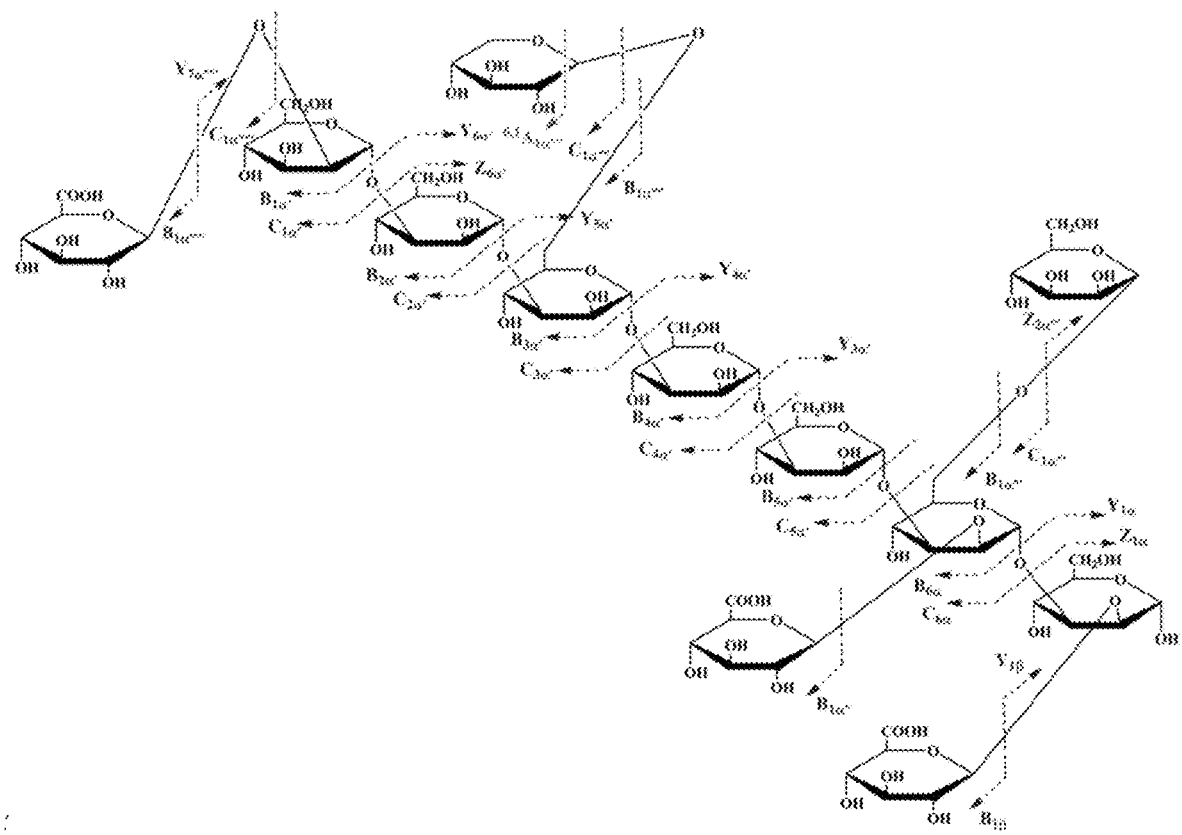
Figure 5C:
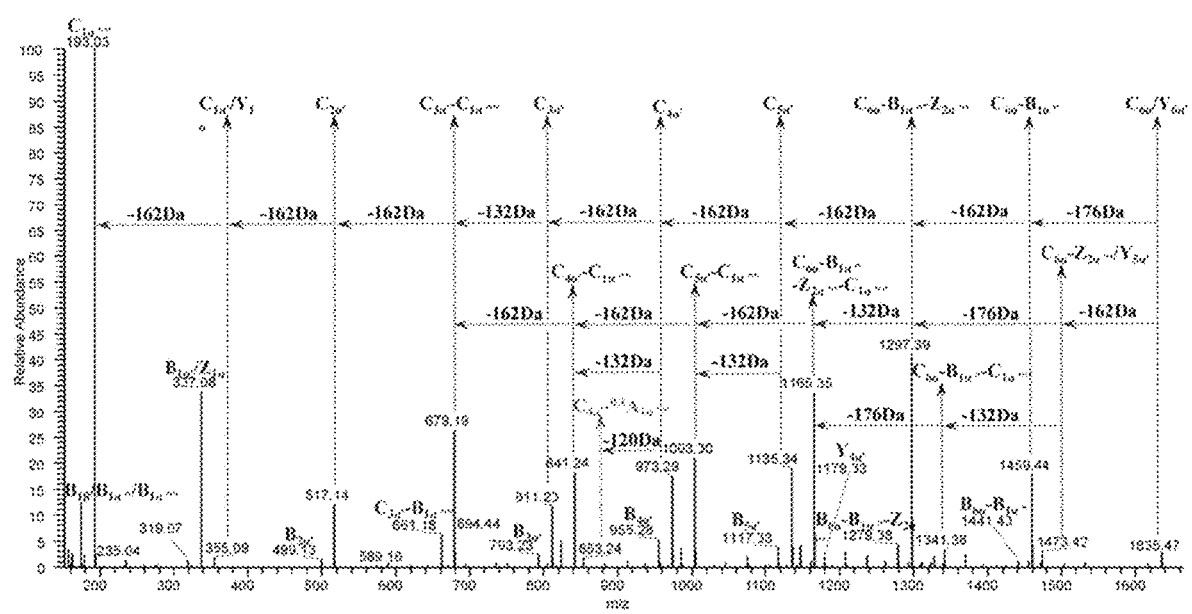

In order to further confirm a chemical fine structure repeating unit of ME-2, the ME-2 was subjected to hydroxyl free radical degradation with a hydrogen peroxide-iron ion system, and a total ion chromatogram was tested by liquid chromatography quadrupole time-of-flight mass spectrometry (LC-QTOF-MS). As shown in Table 1, a total of 18 fragments of the ME-2 resulting from hydroxyl free radical degradation were obtained, and through non-targeted LC-QTOF-MS$^E$ and targeted LC-QTOF-MS/MS techniques, corresponding [M-H]$^-$ and [M-2H]$^{2-}$ were analyzed to determine chemical structures of oligosaccharides and small polysaccharides resulting from the hydroxyl free radical degradation. It should be noted that no acetyl substitution was found in structures of all analyzed free radical degradation products, which may be due to the fact that acetoxy is easily removed during free radical degradation. With a peak 14 as an example, two collision energies were used to specifically elaborate an LC-QTOF-MS/MS identification process of a free radical degradation product. The peak 14 was at a retention time $t_R$=34.67 min, and a molecular weight was determined by [M-2H]$^{2-}$ in LC-QTOF-MS$^1$ to be 986, implying that a polymerization degree was 12, and 8 hexoses, 1 pentose, and 3 hexuronic acids were included (Hex$_8$Pnt$_1$HexA$_3$). As shown in FIGS. 5A-5B, a mass spectrum of a collision energy of 20 eV was used to interpret a precursor ion. The cleavage of a [M-H]$^-$ ion at m/z 1,973 caused continuous losses of 176 Da and 162 Da to obtain m/z 1,797 and 1,635. However, a low collision energy caused the partial doping of a [M-2H]$^{2-}$ ion in [M-H], and thus observations were subsequently conducted with a mass spectrum of a high collision energy. The [M-H]-ion at m/z 1,973 was subjected to targeted cleavage through LC-QTOF-MS/MS, and results were shown in FIG. 5C. The following three main cleavage pathways were obtained in total: (1) m/z 1973→1797→1635→1459→1297→1135→973→811→679→517 (Am: 17→162→176→162→162→162→162→132→162); (2) m/z 1973→1797→1635→1473→1297→1165→1003→841→679→517 (Am: 176→162→162→176→132→162→162→162→162); and (3) m/z 1973→1797→1635→1473→1341→1165→1003→841→679→517 (Am: 176→162→162→132→176→162→162→162→162). Through a neutral loss and a transcyclic cleavage, a structure was determined as shown by peak 14 in Table 1.

TABLE 1

18 fragments of the ME-2 resulting from hydroxyl free radical degradation

| Peaks | $t_R$ | [M − H]$^-$ | [M − 2H]$^{2-}$ | Formula | DP | Low DP saccharides | Key MS/MS fragments (m/z) |
|---|---|---|---|---|---|---|---|
| 1 | 20.60 | 679.23 | — | C$_{24}$H$_{40}$O$_{22}$ | 4 |  | 679, 589, 517, 355, 235, 193 |
| 2 | 22.86 | 811.23 | — | C$_{29}$H$_{48}$O$_{26}$ | 5 | 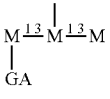 | 811, 721, 679, 517, 355, 235, 193 |
| 3 | 23.58 | 841.24 | — | C$_{30}$H$_{50}$O$_{27}$ | 5 | 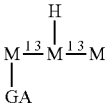 | 841, 751, 679, 589 517, 355, 193 |
| 4 | 24.97 | 973.28 | — | C$_{35}$H$_{58}$O$_{31}$ | 6 | 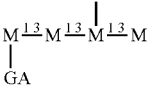 | 973, 883, 841, 811, 679, 517, 355, 193 |
| 5 | 25.54 | 1003.29 | — | C$_{36}$H$_{60}$O$_{32}$ | 6 | 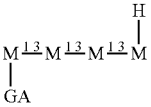 | 1003 913, 883, 841, 679, 517, 355, 193 |
| 6 | 26.06 | 1017.27 | — | C$_{36}$H$_{58}$O$_{33}$ | 6 | 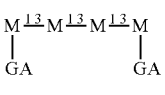 | 1017, 841, 679, 517, 355, 193 |

TABLE 1-continued 18 fragments of the ME-2 resulting from hydroxyl free radical degradation

| Peaks | $t_R$ | $[M-H]^-$ | $[M-2H]^{2-}$ | Formula | DP | Low DP saccharides | Key MS/MS fragments (m/z) |
|---|---|---|---|---|---|---|---|
| 7 | 27.20 | 1149.31 | — | $C_{41}H_{66}O_{37}$ | 7 | M–M–M with X, H substituents; GA, GA | 1149, 973, 841, 811, 679, 517, 355, 337, 193 |
| 8 | 28.39 | 1179.32 | 589.13 | $C_{42}H_{68}O_{38}$ | 7 | M–M–M–M with H; GA, GA | 1179, 1017, 1003, 841, 679, 517, 355, 193 |
| 9 | 29.26 | 1311.34 | 655.15 | $C_{47}H_{76}O_{42}$ | 8 | M–M–M–M–M with X; GA, GA | 1311, 1135, 973, 841, 811, 679, 517, 355, 193, 178 |
| 10 | 29.78 | 1341.38 | 670.15 | $C_{48}H_{78}O_{43}$ | 8 | M–M–M–M–M–M; GA, GA | 1341, 1179, 1165, 1003, 841, 679, 517, 355, 193 |
| 11 | 31.17 | 1635.47 | 817.31 | $C_{59}H_{96}O_{52}$ | 10 | M–M–M–M–M–M–M–M with X; GA, GA | 1635, 1473, 1459, 1297, 1135, 1003, 973, 841, 811, 679, 517, 337, 193 |
| 12 | 34.22 | 1811.32 | 905.25 | $C_{64}H_{104}O_{56}$ | 11 | M–M–M–M–M–M–M–M with X, H; GA, GA, GA | 1811, 1635, 1473, 1459, 1135, 1003, 973, 841, 811, 679, 517, 355, 193 |
| 13 | 34.26 | 1841.35 | 920.25 | $C_{66}H_{106}O_{59}$ | 11 | M–M–M–M–M–M–M–M with H, H; GA, GA, GA | 1841, 1679, 1665, 1503, 1341, 1327, 1003, 841, 679, 517, 337, 193 |
| 14 | 34.67 | 1973.26 | 986 | $C_{71}H_{114}O_{63}$ | 12 | M–M–M–M–M–M–M–M–M with X, H; GA, GA, GA | 1973, 1797, 1635, 1621, 1473, 1459, 1341, 1297, 1165, 1003, 973, 841, 811, 679, 517, 355, 193 |
| 15 | 35.17 | 2105.23 | 1052 | $C_{76}H_{122}O_{67}$ | 13 | M–M–M–M–M–M–M–M–M with X, X, H; GA, GA, GA | 2105, 1943, 1929, 1767, 1605, 1591, 1473, 1297, 1135, 1003, 973, 841, 811, 679, 517, 355, 193 |
| 16 | 35.45 | 2135.26 | 1067 | $C_{77}H_{124}O_{68}$ | 13 | M–M–M–M–M–M–M–M–M with X, H, H; GA, GA, GA | 2135, 1973, 1959, 1797, 1635, 1621, 1503, 1459, 1341, 1165, 1135, 1003, 973, 841, 811, 679, 517, 355, 193 |
| 17 | 35.79 | 2267.31 | 1133.90 | $C_{82}H_{132}O_{72}$ | 14 | M–M–M–M–M–M–M–M–M–M with X, X, H; GA, GA, GA | 2267, 2105, 2091, 1929, 1767, 1635, 1591, 1459, 1135, 1003, 973, 841, 811, 679, 517, 355, 193 |
| 18 | 36.24 | 2297.42 | 1148.89 | $C_{83}H_{134}O_{73}$ | 14 | M–M–M–M–M–M–M–M–M–M with X, H, H; GA, GA, GA | 2297, 2135, 2121, 1959, 1797, 1635, 1621, 1459, 1327, 1297, 1165, 1003, 973, 841, 811, 679, 517, 355, 193 |

Figure 6A:
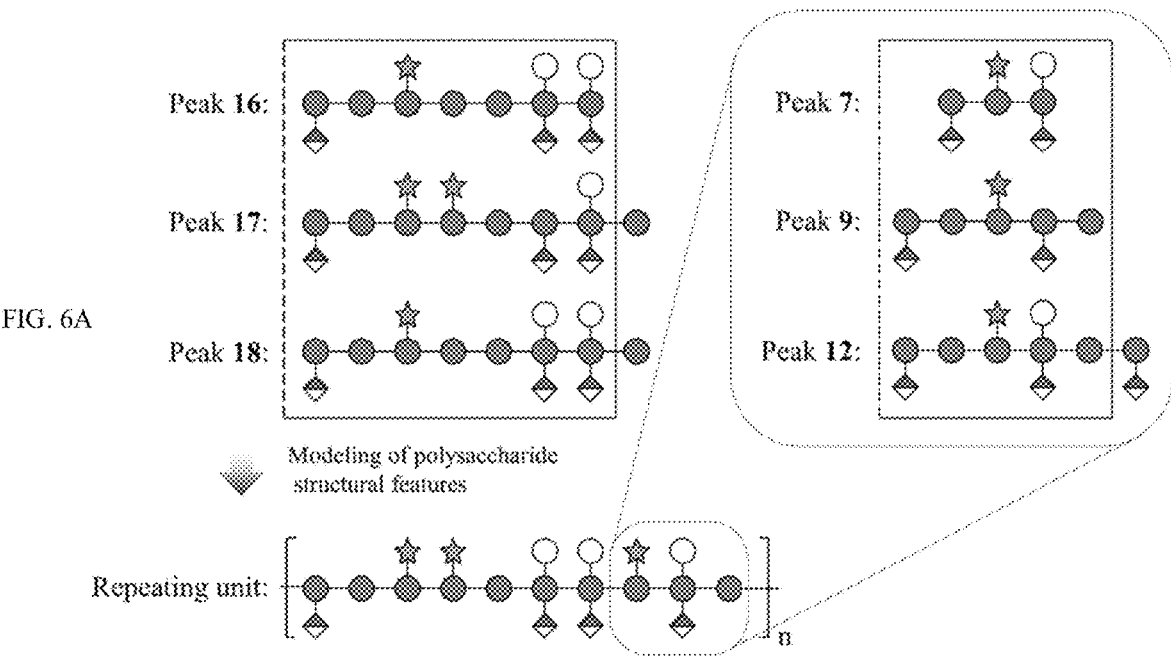
FIGS. 6A-6B are schematic diagrams illustrating deduction of repeating fragments resulting from free radical degradation of the monomeric polysaccharide ME-2 of *A. auricula*.
Figure 6B:
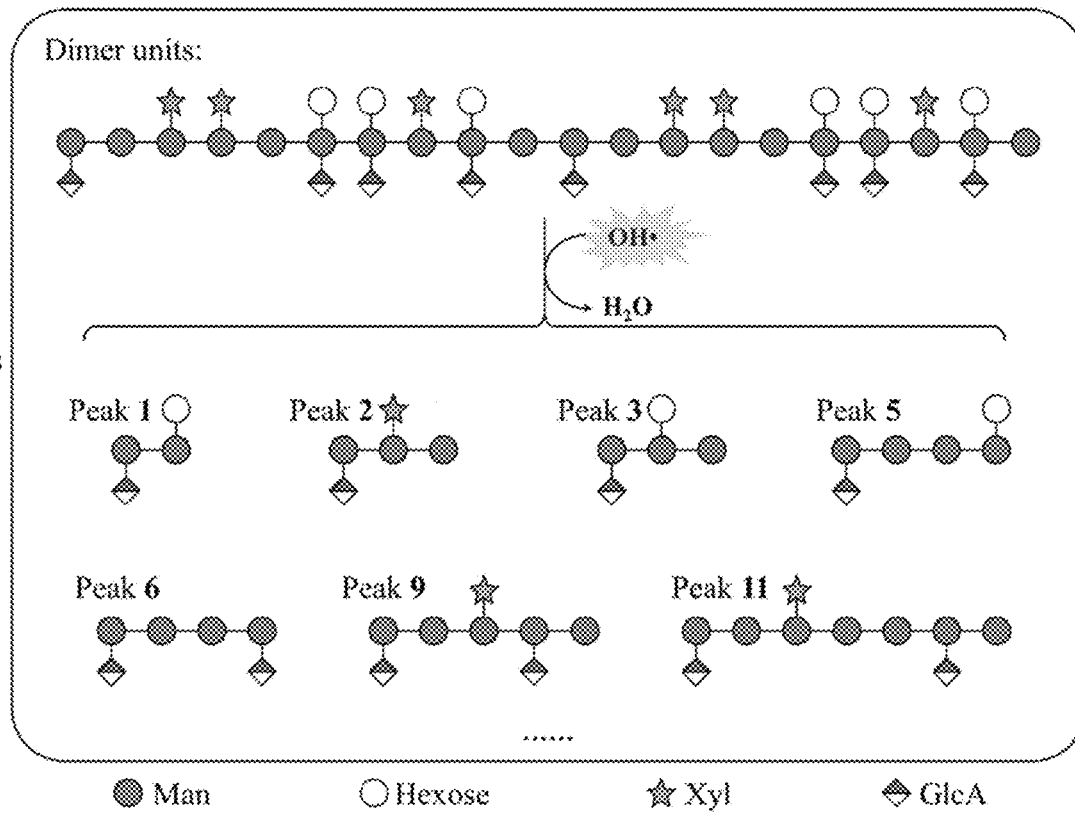
Figure 7A:
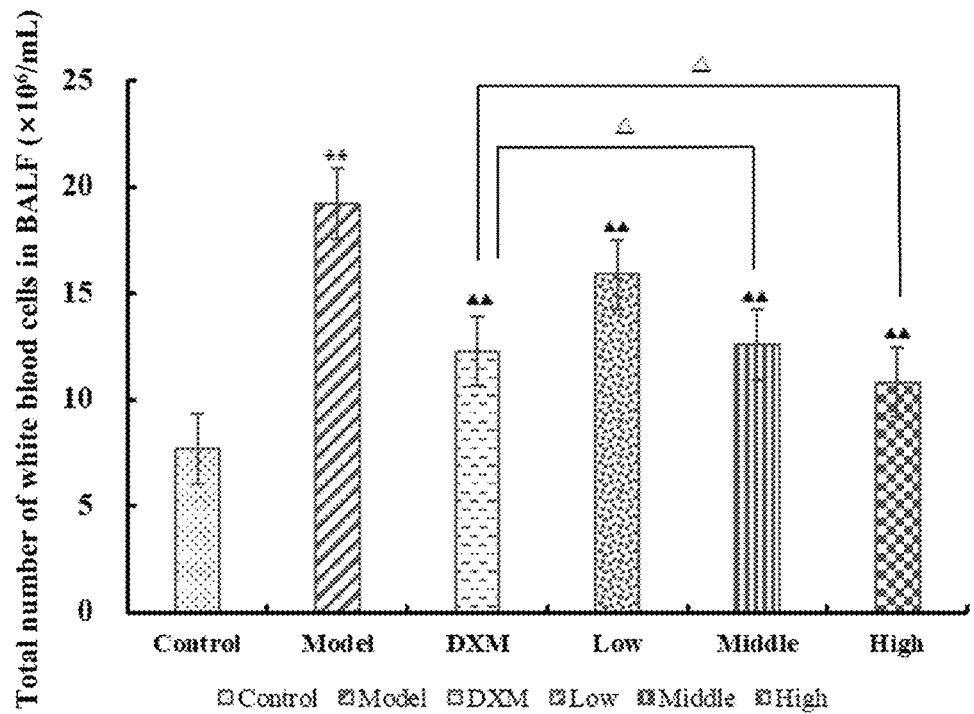
FIGS. 7A-7B show a total number of leukocytes and a percentage of each type of cells in each silicosis mouse model group, where notes: **: $P<0.01$ compared with a control group; ▲▲: $P<0.01$ compared with a model group; and Δ: $P>0.05$ among two groups.
Figure 7B:
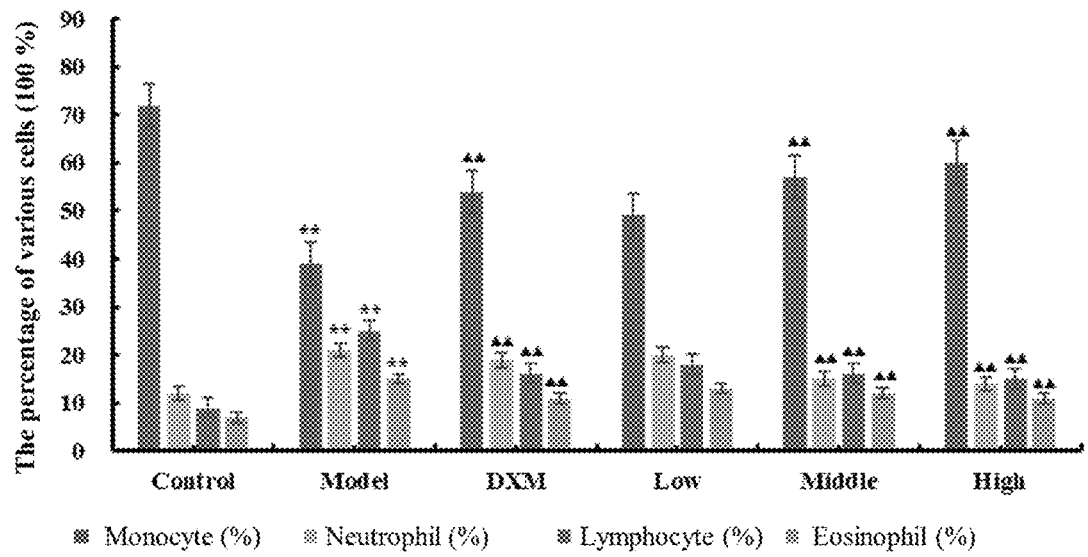
Figure 8A:
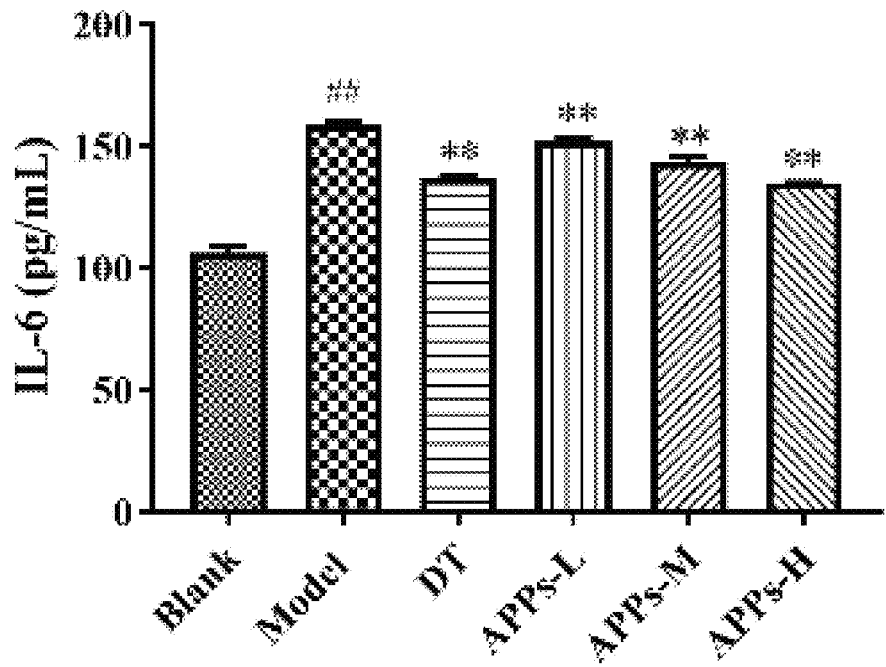
FIGS. 8A-8D show changes of levels of SOD, HYP, IL-6, and TNF-α factors in serum of each silicosis mouse model group detected by enzyme-linked immunosorbent assay (ELISA), where notes: ##: $P<0.01$ compared with a normal control group; **: $P<0.01$ compared with a model group, and Δ: $P>0.05$ among two groups.
Figure 8B:
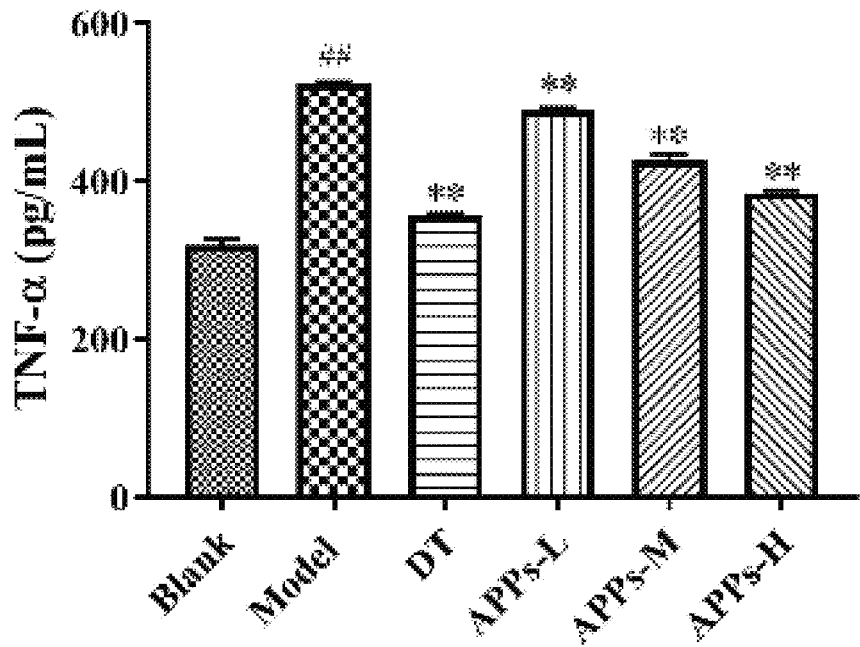
Figure 8C:
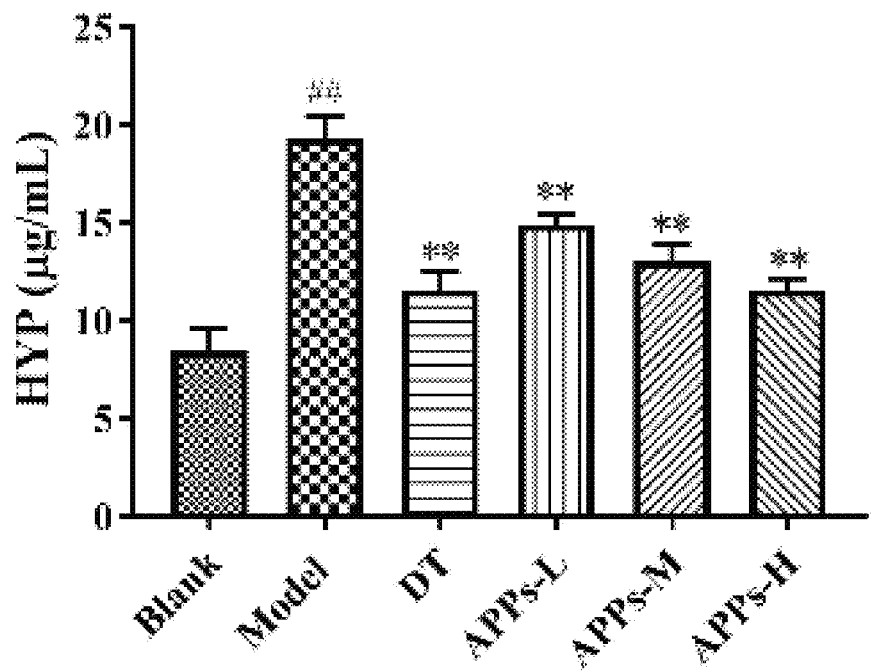
Figure 8D:
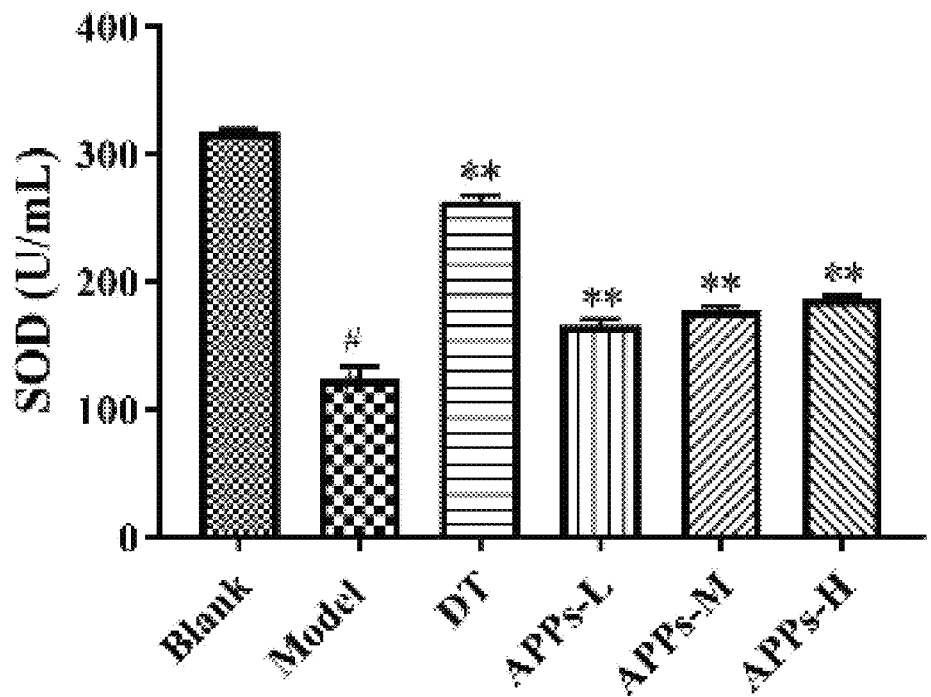
Figure 9A:
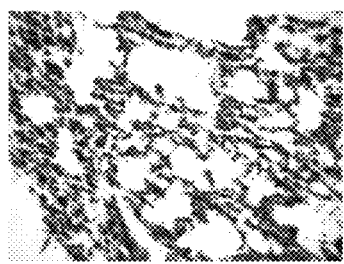
FIGS. 9A-9F show pathological changes of tissues in each silicosis mouse model group detected by hematoxylin and eosin (H&E) staining.
Figure 9B:
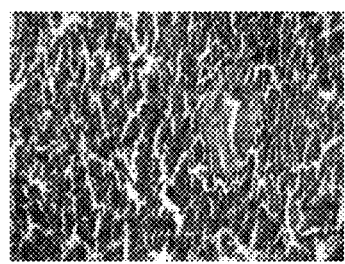
Figure 9C:
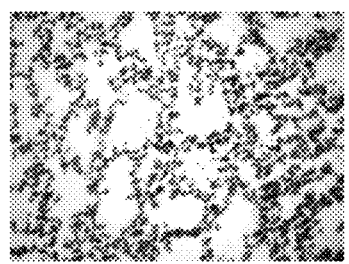
Figure 9D:
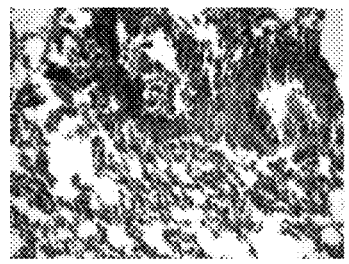
Figure 9E:
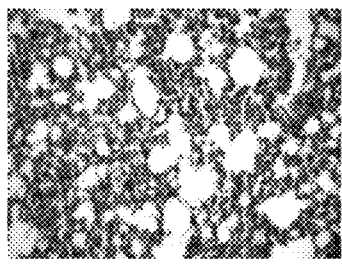
Figure 9F:
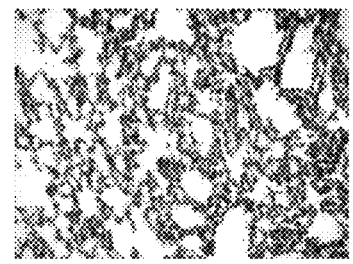
Figure 10A:
FIGS. 10A-10F show pathological changes of tissues in each silicosis mouse model group detected by Masson staining.
Figure 10B:
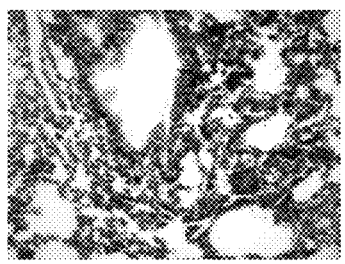
Figure 10C:
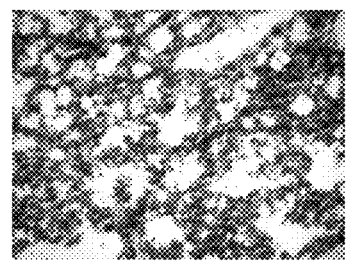
Figure 10D:
Figure 10E:
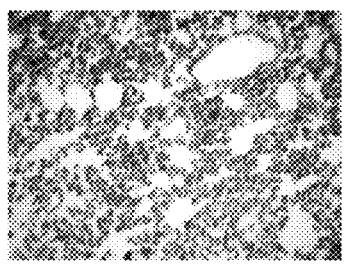
Figure 10F:
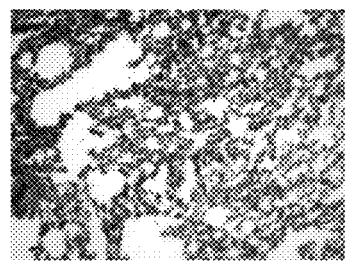

A structure of the ME-2 was subsequently subjected to recombination analysis. As shown in FIG. 6A, the three fragments each included a linear backbone consisting of →3)-Manp-(1→, which meant that left parts of repeating structural units were identical. Right parts of the repeating units could be deduced through modeling according to peaks 7, 9, and 12, and accurate structures of the repeating units could be obtained in combination with the above analysis results. To further verify the accuracy of a repeating unit, all fragments were subjected to degradation simulation. As shown in FIG. 6B, peaks 1 to 18 could be deduced from repeating unit dimers.

Figure 4A:
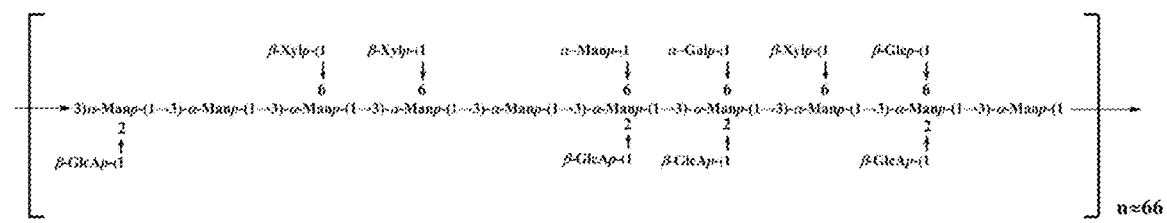
FIGS. 4A-4B show structures of a monomeric polysaccharide ME-2 of *A. auricula* and a deacetylated monomeric polysaccharide ME-2, where
Figure 4B:
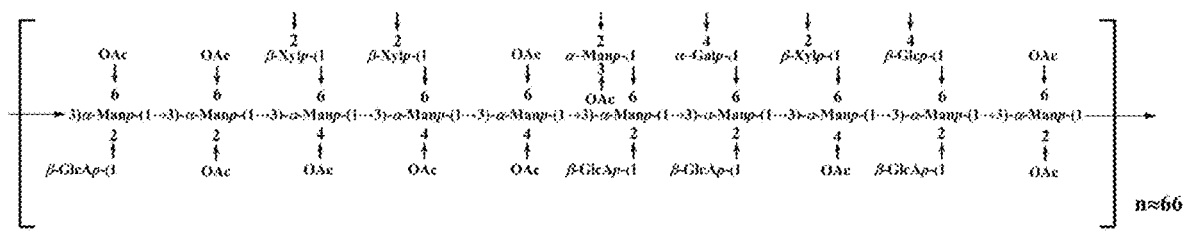

Through various chemical degradation pathways such as monosaccharide composition, methylation analysis, and free radical degradation and various modern instrument methods such as SEC-MALLS-VIS-RID, LC-MRM-MS, LC-QTOF-MS[1], LC-QTOF-MS/MS, GC-MS, $^1$H-NMR, and $^{13}$C-NMR, a chemical finely-structured repeating unit of the d-ME-2 was clearly determined as a structure shown in FIG. 4A. Further, according to a difference between absolute molecular weights before and after deacetylation, it was further concluded that 17 sugar residues in a repeating unit each were substituted with acetyl. According to the above data, a chemical finely-structured repeating unit of the ME-2 was clearly determined as shown below (FIG. 4B):

especially, the release of glycuronic acid may be more difficult than the release of aldohexose. In this way, a high-concentration acid during hydrolysis may cause corresponding losses to aldopentose and aldohexose released during the hydrolysis.

SEC-MALLS-VIS-RID test conditions: A molecular weight ($M_w$) of the ME-2 was determined by HPSEC-MALLS-RID. HPSEC-MALLS-RID was equipped with Waters-e2695 HPLC (Milford, Massachusetts, USA), a Waters-2414 detector (Milford, Massachusetts, USA), a viscosity detector (Goleta, California, USA), and a Wyatt DAWN HelEOS-II MALLS detector (Goleta, California, USA). A chromatographic column was a TSK gel G5000PWXL column (7.8×300 mm, i.d., TOSOH Biosciences, Tokyo, Japan). A mobile phase was a 50 mM ammonium formate aqueous solution, and a flow rate of the mobile phase was 0.5 mL/min. The ME-2 (5 mg) was dissolved in

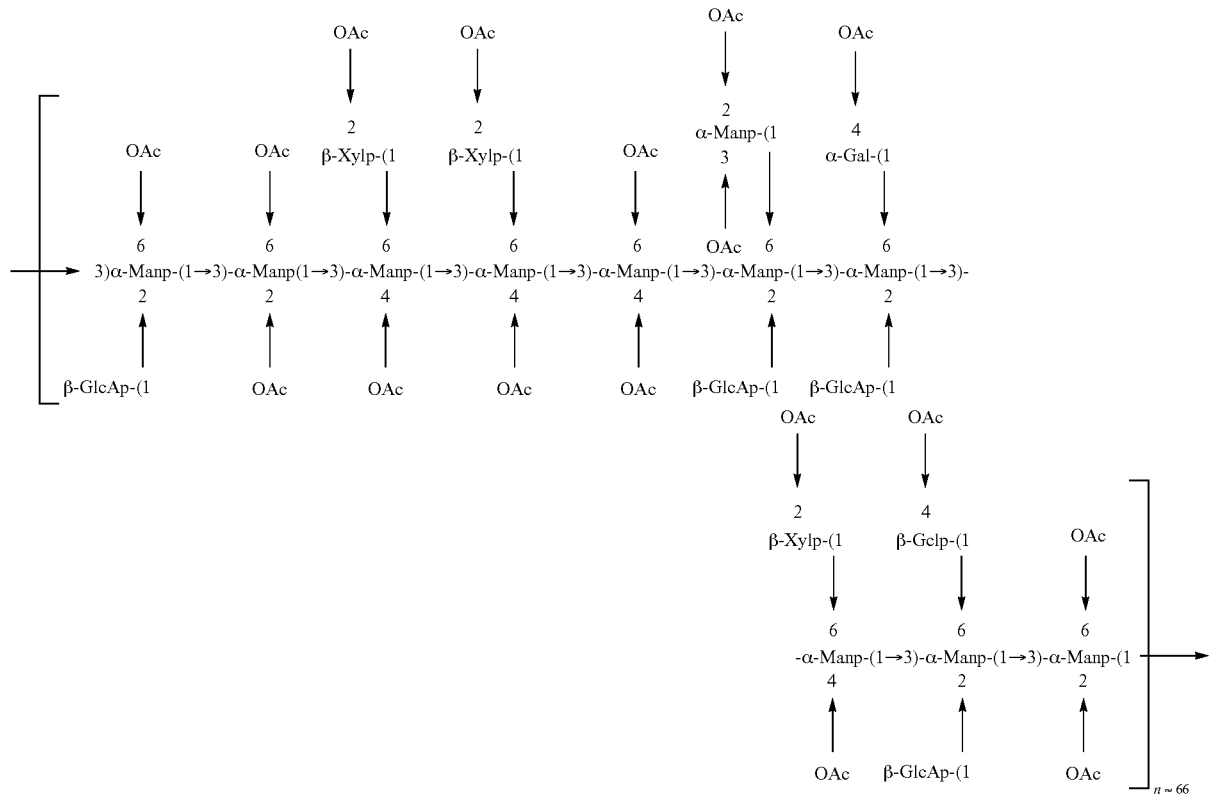

The chemical finely-structured repeating unit of the ME-2 was further analyzed. The ME-2 included the monosaccharides of Xyl, GlcA, Gal, Glc, and Man in a theoretical ratio of 3:4:1:1:11; and the ME-2 included the following residues: →3)-Manp-(1→, →2,3)-Manp-(1→, →2,3,6)-Manp-(1→, →3,6)-Manp-(1→, Manp-(1→, Glcp-(1→, GlcAp-(1→, Xylp-(1→, and Galp-(1→ in a theoretical ratio of 3:1:3:3:1:1:4:3:1. In the experimental monosaccharide composition and sugar residue linkage, a Xyl content was significantly higher than a Xyl content in the theoretical monosaccharide composition and sugar residue linkage, but proportions of Glc, Gal, and GlcA were significantly lower than corresponding proportions in the theoretical monosaccharide composition and sugar residue linkage, which may be attributed to the fact that aldopentose is more easily hydrolyzed and released than aldohexose and glycuronic acid, and 1 mL of the mobile phase, and a resulting solution was centrifuged and then filtered through a 0.22 μm aqueous membrane.

Monosaccharide composition test conditions of LC-MS/MS: The derivatization principle and by-product were analyzed on a Waters C18+ column (150 mm×2.1 mm, 1.6 μm) with an ABSciex Triple TOF 5600+ (Framingham, Massachusetts, USA) and an I-Class UPLC system (Waters, Milford, Massachusetts, USA). A column temperature was set to 35° C., and an injection volume was 5 μL. Mobile phases were 0.1% FA-H2O (A) and 0.1% FA-ACN (B), respectively; and an elution procedure was as follows: 0 min to 8 min, 10% to 90% B, and 0.3 mL/min. In an electrospray ionization (ESI)+ full-scan mode, analysis was conducted from m/z 100-600 Da. Other parameters were as follows: floating ion spray voltage: 4,500.0 V; temperature: 450.0°

C.; curtain gas: 30 L/h; ion source gas (Gas1): 50 L/h; ion source gas (Gas2): 50 L/h; concentration potential (DP): 80 V; and collision energy (CE): 5 V.

Methylation analysis conditions of GC-MS: Agilent 7890A-5975C electron ionization-mass spectrometry (EI-MS); DB-5 capillary column (60 mm×0.25 mm×0.25 μm); programmed heating: a sample was kept at an initial temperature of 120° C. for 2 min, then heated at 4° C./min to 180° C. and kept at this temperature for 2 min, and then heated at 10° C./min to 280° C. and kept at this temperature for 3 min; splitting ratio: 20:1; carrier gas: helium; inlet temperature: 250° C.; column flow rate: 1.2 mL/min; EI (70 eV); interface temperature: 250° C.; ion source temperature: 230° C.; scanning range: m/z 50-550; and scanning rate: 2.5 scan/s.

Free radical degradation test conditions of LC-QTOF-MS/MS: A negative ion mode of a Waters ACQUITY UPLC/Xevo G2XS QTOF LC-MS and a BEH Amide chromatographic column (2.1×100 mm, 1.8 μm) were adopted. A mobile phase A was a 0.1% formic acid (v/v) aqueous solution, and a mobile phase B was a 0.1% formic acid (v/v) acetonitrile solution. Elution of a UHPLC system was as follows: 0 min to 25 min, 90%-50% B; 25 min to 28 min, 50%-50% B; and 28 min to 30 min, 50%-90% B. A column flow rate was 0.3 mL/min, a column temperature was holden at 35° C., a sample chamber temperature was set to 10° C., an injection volume was 5 μL, and a scanning range was m/z 100-3,000 Da.

Test Example 1 Test on a Protective Effect of the Monomeric Polysaccharide ME-2 of *A. auricula* for Silicosis Mice I. Test Method Healthy clean BALB/c mice were randomly divided into experimental groups with 10 mice in each group. Preparation of a mouse silicosis model with a self-braking dust modeling device: Mice in groups other than a blank group were placed in a dust box, and a specified amount of a $SiO_2$ dust was weighed and blown by a blower into the dust box to adjust a dust mass concentration in the dust box to 125 mg/m$^3$. A dust molding time was 21 d. After a test was completed, the mice each were intraperitoneally injected with 5% chloral hydrate for anesthesia, and then sacrificed; eyeballs were taken, and blood was collected; endotracheal intubation was conducted, 0.8 mL of phosphate buffered saline (PBS) was injected into lungs, and a bronchoalveolar lavage fluid (BALF) was repeatedly collected; and organs such as lungs, spleen, and pancreas were collected from the mice.

Differential cell counting of BALF: A precipitate obtained after centrifugation of BALF was resuspended with 1 mL of PBS, 50 μL of a resulting suspension was taken and added to a hemocytometer, and a number of cells was measured under an optical microscope; and 0.1 mL of the suspension was taken, smeared, and subjected to Wright-Giemsa staining, and the differential cell counting of eosinophils, lymphocytes, neutrophils, or the like was conducted. About 3 replicates were set, and an average was taken.

The levels of IL-6, TNF-α, SOD, and HYP factors were detected by ELISA according to instructions of a kit, and specific operations were as follows: (1) A plate was taken, 50 μL of a standard was added to each standard well at different concentrations, 10 μL of serum and 40 μL of a sample diluent were added to a sample well, and the plate was incubated in a 37° C. incubator for 0.5 h. (2) \ supernatant in each well was completely removed; each well was filled with a washing liquid to allow a reaction for 1 min, then the washing liquid was discarded, then a washing liquid was added once again, and this washing process was repeated 5 times; and an ELISA reagent was added, and the plate was incubated in a 37° C. incubator for 0.5 h. (3) A supernatant in each well was completely removed; each well was filled with a washing liquid to allow a reaction for 1 min, then the washing liquid was discarded, then a washing liquid was added once again, and this washing process was repeated 5 times; and chromogenic solutions A and B were added, and the plate was incubated in a 37° C. incubator for 10 min. (4) 50 μL of a stop solution was added to each well, and then an OD value corresponding to each well was immediately detected at a wavelength of 450 nm. (5) According to the original concentrations of the standards and corresponding values thereof, a linear regression equation of a standard curve was listed, and then a concentration of a sample was calculated through the equation according to a value of the sample on the curve.

Paraffin embedding: 1. Fixation: A fresh tissue was fixed with 4% paraformaldehyde (PFA) in PBS (PH: 7.2 to 7.6) for 24 h. 2. Paraffin embedding: A fixed tissue was cut into 0.5×0.3×0.3 cm tissue blocks, and then subjected to dehydration, permeabilization, waxing, and embedding according to the following methods. (1) The tissue blocks were rinsed with running water for 30 min to remove the excess fixing solution. (2) Dehydration: The tissue blocks were soaked in each of 70% alcohol, 80% alcohol, 90% alcohol, 100% alcohol (I), and 100% alcohol (II) for 40 min. (3) Permeabilization: The tissue blocks were soaked in xylene (I) for 15 min and in xylene (II) for 10 min. (4) Waxing: The permeabilized tissue blocks were placed in each of melted paraffin (I), melted paraffin (II), and melted paraffin (III) in an incubator for 40 min. (5) Embedding: The soaked tissue blocks were embedded for sectioning.

HE staining: 1. The embedded tissue was sectioned, dewaxed, and placed in each of xylene solutions I and II to allow a reaction for 5 min. 2. Washing with ethanol at a series of concentrations and water: A sample was washed with 100% ethanol for 2 min, with 95% ethanol for 1 min, with 90% ethanol for 1 min, with 85% ethanol for 1 min, and with distilled water for 1 min. 3. The sample was treated with hematoxylin for 10 min and then rinsed with purified water for 2 min. 4. The sample was subjected to differentiation with 75% ethanol hydrochloride for 30 s. 5. The sample was soaked in tap water for 15 min. 6. The sample was stained with eosin for 1 min. 7. The sample was subjected to conventional dehydration, permeabilization, and mounting: The sample was subjected to a reaction in each of 95% ethanol (I) and (II), 100% ethanol (I) and (II), xylene/carbolic acid (3:1), and xylene (I) and (II) for 1 min, and finally mounted with a neutral resin.

Masson staining: 1. A sample was subjected to paraffin sectioning and dewaxing. 2. The sample was subjected to a chromation treatment or mercury salt precipitate removal (this step could be omitted for a formaldehyde-fixed tissue). 3. The sample was washed with tap water and distilled water successively. 4. The sample was subjected to nuclear staining with a Regaud hematoxylin staining solution or a Weigert hematoxylin staining solution for 5 min to 10 min. 5. The sample was fully washed, and if there was excessive staining, the sample was subjected to differentiation with ethanol hydrochloride. 6. The sample was washed with distilled water. 7. The sample was stained with a Masson Ponceau S acid fuchsin stain for 5 min to 10 min. 8. The sample was soaked in a 2% glacial acetic acid aqueous solution for a while. 9. The sample was subjected to differentiation with a 1% phosphomolybdic acid aqueous solution for 3 min to 5 min. 10. The sample was directly stained with an aniline blue or glossy green solution for 5 min. 11. The sample was soaked in a 0.2% glacial acetic acid aqueous solution for a while. 12. The sample was permeabilized in 95% alcohol, anhydrous alcohol, and xylene, and then mounted with a neutral gum.

II. Test Results

It can be seen from comparison of cell percentages in BALF among silicosis mouse model groups that, compared with a model group, percentages of eosinophils, neutrophils, and lymphocytes in high-dose and medium-dose groups of the monomeric polysaccharide ME-2 of *A. auricula* are significantly reduced.

ELISA test results show that, after administration of the monomeric polysaccharide ME-2 of *A. auricula*, the levels of oxidative and inflammatory factors such as SOD, HYP, IL-6, and TNF-α that are increased due to modeling can be significantly reduced in a dose-dependent manner.

HE and Masson staining results show that red blood cells (RBCs) are scattered in alveoli of mice in the model group, and after mice in each group were administered with the monomeric polysaccharide ME-2 of *A. auricula*, the above pathological state changes to varying degrees, where RBCs scattered in the alveoli are reduced in a dose-dependent manner, a positive drug effect is prominent, and there is connective tissue proliferation; the medium-dose and high-dose groups of the monomeric polysaccharide of *A. auricula* have an optimal change effect; and in the low-dose group, there are local inflammatory cell spheres, partial alveolar dilatation, and a large number of foreign bodies in tracheas.

What is claimed is:

1. A method for isolating a polysaccharide from an *Auricularia auricula-judae* (*A. auricula*), wherein the polysaccharide is a high-acetyl glucuronoxylogalactoglucomannan with a molecular weight of 260 kDa and an acetyl content of 18%; the polysaccharide comprises xylose (Xyl), glucuronic acid (GlcA), galactose (Gal), glucose (Glc), and mannose (Man), and the Xyl, the GlcA, the Gal, the Glc, and the Man are in a molar ratio of 3:4:1:1:11; wherein the polysaccharide comprises a chemical finely-structured repeating unit of the polysaccharide is as follows:

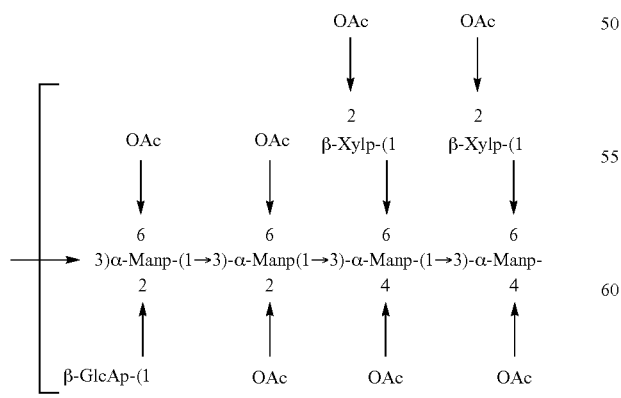

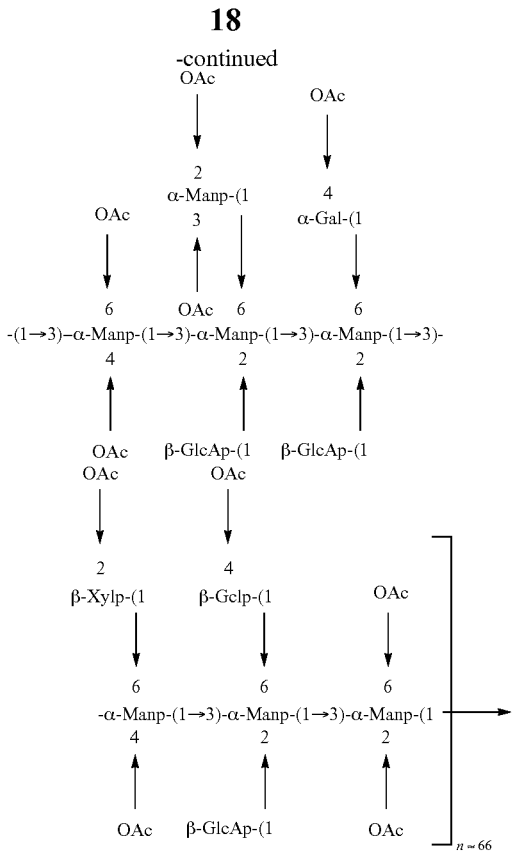

the method comprising:
(1) with water as an extraction solvent, conducting a heat reflux extraction (HRE) on the *A. auricula* to obtain an *A. auricula* extract-containing aqueous solution;
(2) subjecting the *A. auricula* extract-containing aqueous solution to an adsorption with an AB-8 macroporous adsorption resin column to remove pigments and proteins, and subjecting the AB-8 macroporous adsorption resin column to a first elution with an eluent to obtain an *A. auricula* extract-containing aqueous eluate; wherein the eluent is a first distilled water, and during the first elution, the first distilled water is used at an amount six times a volume of the AB-8 macroporous adsorption resin column;
(3) subjecting the *A. auricula* extract-containing aqueous eluate to an treatment with a 3 kDa ultrafiltration (UF) chromatographic column to obtain refined total polysaccharides of the *A. auricula*; and
(4) treating the refined total polysaccharides of the *A. auricula* with an Amber-lite FPA90-Cl⁻ anion exchange resin column to obtain a refined polysaccharide of the *A. auricula*, wherein a second elution is conducted with a second distilled water in a volume four times a volume of the Amber-lite FPA90-Cl⁻ anion exchange resin column and 1 mol/L NaCl in a volume two times the volume of the Amber-lite FPA90-Cl⁻ anion exchange resin column, and an eluate of the distilled water is collected to obtain the refined polysaccharide of the *A. auricula*; and subjecting the refined polysaccharide to a refinement and a purification with a DEAE-650M anion exchange chromatographic column to obtain the polysaccharide, wherein a third elution is conducted with a third distilled water and 0.5 mol/L NaCl, and an eluate of the 0.5 mol/L NaCl is collected to obtain the polysaccharide.

* * * * *